US012612576B1

(12) United States Patent
Almodafar

(10) Patent No.: US 12,612,576 B1
(45) Date of Patent: Apr. 28, 2026

(54) PRODUCTION OF OILS FROM PALM BARK

(71) Applicant: KING FAISAL UNIVERSITY, Al-Ahsa (SA)

(72) Inventor: Fuad Ahmad Saleh Almodafar, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/440,238

(22) Filed: Feb. 13, 2024

(51) Int. Cl.
  *A61K 36/889* (2006.01)
  *A61K 8/9794* (2017.01)
  *C11B 1/10* (2006.01)

(52) U.S. Cl.
  CPC .............. *C11B 1/10* (2013.01); *A61K 8/9794* (2017.08); *A61K 36/889* (2013.01)

(58) Field of Classification Search
  None
  See application file for complete search history.

(56) References Cited

PUBLICATIONS

Doing, Red palm oil extraction process, www.palmoilextractionmachine.com; 2024.

Mohd Sharizan Md Sarip, et al., "Composition of Crude Palm Oil Extracted Using Hot Compressed Water Extraction" DOI: 10.5650/jos.ess22248; Jan. 2023.

Henan Doing, Nigeria different palm oil extraction methods and its features, www.edibleoilextractionmachine.com; 2024.

Aizuddin Abdul Rahman, et al "Temperature Effect on the Characterization of Pyrolysis Products from Oil Palm Fronds", www.seipub.org/aee, Advances in Energy Engineering (AEE) vol. 2 Issue 1, Jan. 2014.

*Primary Examiner* — Russell G Fiebig
(74) *Attorney, Agent, or Firm* — Nath, Goldberg & Meyer; Joshua B. Goldberg

(57) ABSTRACT

The present subject matter relates to a method of extracting palm pollen oil from palm tree bark and using the oil for various purposes including cosmetics, nutritional supplements, traditional medicine, culinary uses, and animal feed.

5 Claims, No Drawings

PRODUCTION OF OILS FROM PALM BARK

BACKGROUND

1. Field

The disclosure of the present patent application relates to a method of extracting palm pollen oil from palm bark and methods of using said palm pollen oil.

2. Description of the Related Art

Palm trees are a unique plant because they do not have conventional flowers like most plants. Instead, palm trees produce inflorescences, spikes, or panicles as blooms. The size, shape, and color of these blooms can vary depending on the type of palm tree.

Both male and female flowers of palm trees, numbering in the hundreds, are borne on thin structures called rachillae or strands. The rachillae are borne on flat, tapering peduncles (also called rachises) originating in the axis of leaves developed during the previous growing season. These peduncles are referred to as fruit bunch stalks or fruit stalks on female trees. These structures constitute the inflorescences of the date palm.

The primary source of palm oil is the fruit of the oil palm tree (*Elaeis guineensis*), which is rich in oil content. The palm oil industry has faced criticism for its environmental impact, including deforestation and habitat destruction. Therefore, sustainable practices and responsible sourcing are crucial considerations for any palm-derived product, including palm bark utilization.

Thus, a new solution to use other parts of the palm tree is desired.

SUMMARY

Palm bark is not technically "bark" at all. Palm bark is made of "sclerified", or hardened cells left over from bases of previously shed fronds. This makes a palm tree not unlike a column of reinforced concrete with the vessels acting as rebar.

Palm bark can be utilized to produce bioenergy through processes such as pyrolysis or gasification. These processes involve heating the bark in the absence of oxygen to produce biofuels like bio-oil or syngas, which can be used for energy generation or further refined into transportation fuels.

Additionally, palm bark can be used as a raw material in the production of wood-based products such as pulp and paper, particleboard, or fiberboard. The bark is typically removed during the processing of palm fruit, and its utilization in other industries can help reduce waste and maximize resource efficiency.

Palm pollen oil as described herein is extracted from the pollen extracted from the bark surrounding the date of date palms. The oil can be extracted through an evaporation technique or through other methods. The oil may then be divided into two species. A first type of oil may be used as a monoscent perfume oil that can be used in the perfume industry. A second type of oil may be used to treat skin or joints. Other treatments with the second type of oil are also possible.

The present subject matter relates to a method of extracting pollen oil from palm bark rather than from palm fruit such as coconuts.

The present subject matter relates to a method of extracting oil from palm bark, the method comprising: collecting the palm bark; washing the palm bark in a container; cutting and cooking the palm bark in water to obtain concentrated palm pollen water; heating the concentrated palm pollen water with the palm bark; condensing steam coming from the concentrated palm pollen water through a tube; distilling resulting water to obtain palm pollen water; and extracting pollen oil from the palm pollen water to obtain extracted pollen oil.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Palm bark is made of "sclerified", or hardened, cells left over from bases of previously shed fronds. This makes a palm tree not unlike a column of reinforced concrete with the vessels acting as rebar. Palm bark can be utilized to produce bioenergy through processes such as pyrolysis or gasification. These processes involve heating the bark in the absence of oxygen to produce biofuels like bio-oil or syngas, which can be used for energy generation or further refined into transportation fuels.

Additionally, palm bark can be used as a raw material in the production of wood-based products such as pulp and paper, particleboard, or fiberboard. The bark is typically removed during the processing of palm fruit, and its utilization in other industries can help reduce waste and maximize resource efficiency.

Palm pollen oil as described herein is extracted from the pollen extracted from the bark surrounding the date of date palms. The oil can be extracted through an evaporation technique or through other methods. The oil may then be divided into two species. A first type of oil may be used as a monoscent perfume oil that can be used in the perfume industry. A second type of oil may be used to treat skin or joints. Other treatments with the second type of oil are also possible.

Extracting palm pollen oil typically involves several steps. A general overview of the involved process includes harvesting, drying, pollen separation, oil extraction, filtration, purification, and storage.

Harvesting: Palm pollen may be collected from the male flowers of palm trees. The male flowers are usually cut and collected when they are fully mature and about to release pollen.

Drying: The collected male flowers may be dried in a well-ventilated area or under controlled conditions to reduce moisture content. This step helps in preserving the quality of the pollen and preventing the growth of microorganisms.

Pollen Separation: Once the flowers are dried, the pollen needs to be separated from the plant material. This can be done through various methods such as sieving, shaking, or using specialized equipment like pollen extractors. The goal is to obtain pure pollen without any impurities.

Oil Extraction: There are different methods to extract oil from palm pollen, including solvent extraction, cold pressing, and supercritical fluid extraction.

Solvent Extraction: In this method, a solvent such as hexane may be used to dissolve the oil from the pollen. The mixture may then be filtered to separate the solvent from the oil. The solvent is evaporated, leaving behind the palm pollen oil.

Cold Pressing: Cold pressing involves applying mechanical pressure to the pollen to extract the oil. This method may typically be used for oils that can be easily extracted without the need for heat. The pollen is pressed using a hydraulic press or an expeller, and the oil is collected.

Supercritical Fluid Extraction: Supercritical fluid extraction utilizes a fluid, such as carbon dioxide, in its supercritical state to extract the oil. Supercritical fluid acts as a solvent to dissolve the oil from the pollen. After extraction, the fluid is depressurized, and the oil is separated.

Filtration and Purification: Once the oil is extracted, it may undergo filtration to remove any remaining impurities or particulate matter. This step helps to obtain a cleaner and more refined oil.

Storage: The extracted palm pollen oil is stored in appropriate containers, away from light and heat, to maintain its quality and prevent oxidation.

The present subject matter relates to a method of extracting palm pollen oil from palm bark, the method comprising: collecting the palm bark; washing the palm bark in a container; cutting and cooking the palm bark in water to obtain concentrated palm pollen water; heating the concentrated palm pollen water with the palm bark; condensing steam coming from the concentrated palm pollen water through a tube; distilling resulting water to obtain palm pollen water; and extracting pollen oil from the palm pollen water to obtain extracted pollen oil.

In an embodiment of the present subject matter, the palm bark and the water may be added in a ratio of 1 kilogram to 2.5 liters.

In another embodiment of the present subject matter, 60 kilograms of the palm bark may yield 16 liters of the extracted palm pollen water.

In a further embodiment, two species of oil may be extracted.

In an embodiment, the extracted pollen oil may be used as a fragrance oil.

In another embodiment, the extracted pollen oil may be used for therapeutic purpose, such as by way of non-limiting example, a joint oil to aid in joint pain, a skincare oil, and various other uses typical of plant-based oils.

Pollen oil has various applications in the cosmetic, pharmaceutical, and nutritional industries. Common uses include:

Cosmetics: Pollen oil is known for its nourishing and moisturizing properties, making it a popular ingredient in skincare and haircare products. It can be found in creams, lotions, serums, masks, and shampoos, contributing to hydration, softness, and improved skin and hair health.

Nutritional Supplements: Pollen oil is rich in nutrients, including vitamins, minerals, amino acids, and fatty acids. It is often used as a dietary supplement in the form of capsules or oils. It is believed to provide various health benefits, such as supporting immune function, promoting energy, and aiding in overall well-being.

Traditional Medicine: In some traditional medicine practices, pollen oil is used for its potential therapeutic properties. It may be consumed orally or applied topically for its purported anti-inflammatory, antioxidant, and anti-aging effects. However, it's important to note that scientific evidence supporting these claims is limited, and further research is needed.

Culinary Uses: Pollen oil can be used in culinary applications, particularly for adding flavor and nutritional value. It can be drizzled over salads, used as a dressing ingredient, or incorporated into sauces and marinades. However, due to its relatively high cost and limited availability, pollen oil is not commonly used in everyday cooking.

Animal Feed: Pollen oil is sometimes included in animal feed formulations, especially for livestock and honeybees. It serves as a source of nutrients and can contribute to the overall health and productivity of the animals.

In a further embodiment, the method may include removing additional palm oil that clings to the sides of the container.

The following examples illustrate the present teachings.

Example 1

Method for Extracting Palm Pollen Oil from Palm Bark

Pollen oil is extracted from the palm pollen water. The palm frond cover is cut and cooked to extract the concentrated palm pollen water. Palm pollen water is one of the many uses of the palm tree. The palm frond cover is locally known as "Al-Garuf" or "Al-Taltal" and is widely used in the Arabian Gulf countries. The production of palm pollen water is considered a traditional popular industry in the Kingdom and the Arabian Gulf.

After palm pollination, the frond covers are collected, washed with water, and then cut into small pieces. These pieces are placed in a metal pot with water and a tight lid. The diameter of this pot is close to half a meter.

The water is heated until it reaches the boiling point, and then the evaporation process takes place. The steam turns into water saturated with the aroma and taste of the palm frond cover. A metal tube connected to the pot passes through a cold-water pool to cool and condense the steam. Then, this tube ends in a large bottle or several bottles where the palm pollen water is distilled after being cooled.

The approximate weight of the quantity of palm frond covers placed in the metal pot is sixty kilograms.

Typically, from the sixty kilograms of palm frond covers, approximately sixteen liters of palm pollen water are produced. From sixteen liters of palm pollen water, approximately five grams of fragrant pollen oil are produced, and this amount increases further after emptying the container that contains the palm pollen water. The oil clings to the walls of the container and accumulates at the bottom of the container after several hours of emptying it from the palm pollen water. Its weight ranges from 8 grams to 10 grams.

It is to be understood that the method of extracting palm oil from palm bark described herein is not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of extracting pollen oil from *Elaeis guineensis* palm bark, the method comprising:
   (a) collecting the palm bark comprising pollen;
   (b) washing the palm bark in a container;
   (c) cutting and heating the palm bark in water to obtain concentrated palm pollen water;
   (d) heating the concentrated palm pollen water with the palm bark, and condensing steam coming from the concentrated palm pollen water through a tube;
   (e) distilling the resulting water to obtain distilled palm pollen water; and
   (f) extracting pollen oil from the distilled palm pollen water.

2. The method of claim 1, wherein the palm bark and the water are added in a ratio of 1 kilo gram to 2.5 liters.

3. The method of claim 1, wherein 60 kilograms of the palm bark yields 16 liters of the extracted palm pollen water.

4. The method of claim 3, wherein the 16 liters of the palm pollen water yields 5 grams of pollen oil.

5. The method of claim 1, further comprising:
   (g) emptying the container; and
   (h) removing pollen oil clinging to sides of the container.

* * * * *